(12) United States Patent
Ceballos

(10) Patent No.: US 11,559,063 B2
(45) Date of Patent: Jan. 24, 2023

(54) METHODS AND SYSTEMS FOR ENHANCING FEED-CONVERSION-RATIO IN ANIMALS USING MOBILE ENZYME SEQUESTRATION PLATFORMS (MSEP)

(71) Applicant: BOARD OF TRUSTEES OF THE UNIVERSITY OF ARKANSAS, Little Rock, AR (US)

(72) Inventor: Ruben Michael Ceballos, Farmington, AR (US)

(73) Assignee: BOARD OF TRUSTEES OF THE UNIVERSITY OF ARKANSAS, Little Rock, AR (US)

( * ) Notice: Subject to any disclaimer, the term of this patent is extended or adjusted under 35 U.S.C. 154(b) by 143 days.

(21) Appl. No.: 17/324,376

(22) Filed: May 19, 2021

(65) Prior Publication Data

US 2021/0360944 A1 Nov. 25, 2021

Related U.S. Application Data

(60) Provisional application No. 63/026,876, filed on May 19, 2020.

(51) Int. Cl.
| | |
|---|---|
| *A23K 10/14* | (2016.01) |
| *C07K 14/00* | (2006.01) |
| *C12N 9/24* | (2006.01) |
| *C12N 9/16* | (2006.01) |
| *A23K 20/189* | (2016.01) |
| *A23K 20/163* | (2016.01) |
| *A23K 20/147* | (2016.01) |
| *A23K 50/75* | (2016.01) |

(52) U.S. Cl.
CPC ............ *A23K 10/14* (2016.05); *A23K 20/147* (2016.05); *A23K 20/163* (2016.05); *A23K 20/189* (2016.05); *A23K 50/75* (2016.05); *C07K 14/00* (2013.01); *C12N 9/16* (2013.01); *C12N 9/2482* (2013.01); *C12Y 301/03008* (2013.01); *C12Y 302/01008* (2013.01); *C07K 2319/00* (2013.01)

(58) Field of Classification Search
CPC .................. C12Y 302/01001; A23K 50/60
See application file for complete search history.

(56) References Cited

U.S. PATENT DOCUMENTS 11,008,534 B2 * 5/2021 Ayangbile ...... C12Y 302/01001

* cited by examiner

*Primary Examiner* — Tekchand Saidha
(74) *Attorney, Agent, or Firm* — Locke Lord LLP; Tim Tingkang Xia, Esq.

(57) ABSTRACT

A method for enhancing the enzymatic efficiency of an enzyme added to poultry feed for a living subject, comprises adding a cellulose-degrading enzyme to a mobile enzyme sequestration platform (MESP) so as to form an enzyme-MESP complex; adding the enzyme-MESP complex to poultry feed for a living subject; the enzyme efficiency of the cellulose-degrading enzyme of the enzyme-MESP complex after being exposed to a first adverse environment for a first period of time is at least 50% higher than the enzyme efficacy of the cellulose-degrading enzyme independent of the MESP being exposed to the first adverse environment for the first period of time.

18 Claims, 6 Drawing Sheets

Specification includes a Sequence Listing.

-Prior Art-

METHODS AND SYSTEMS FOR ENHANCING FEED-CONVERSION-RATIO IN ANIMALS USING MOBILE ENZYME SEQUESTRATION PLATFORMS (MSEP)

CROSS-REFERENCE TO RELATED APPLICATION

This application claims priority to and the benefit of U.S. Provisional Patent Application No. 63/026,876, filed May 19, 2020, which is incorporated by reference herein in its entirety.

STATEMENT AS TO RIGHTS UNDER FEDERALLY-SPONSORED RESEARCH

This invention was made with government support under grant numbers 1856091 and 1818346 awarded by the National Science Foundation. The government has certain rights in the invention.

FIELD OF THE INVENTION

The invention relates to a system, methodology or formula for enhancing feed-conversion-ratio (FCR) in animals, particularly, in the poultry and herd industry, using mobile enzyme sequestration platforms.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Feed conversion ratio (FCR) is an important factor reflecting the growth performance of animals in animal and poultry industry. It is a ratio or rate measuring of the efficiency with which the bodies of animals convert animal feed into the desired output. For animals raised for meat (such as beef cows, pigs, chickens, and fish), the output is the flesh. That is, the body mass gained by feeding, represented either in the final mass of the animal or the mass of the dressed output. FCR is determined by the animal's genetics and age, the quality and ingredients of the feed, the conditions in which the animal is kept, and storage and use of the feed by the farmworkers. To enhance the FCR, addictive and/or supplement are frequently added into feeds for animals. These addictive and/or supplement may comprise enzymes which are designed to assist breakdown of the feeds in a more timely and efficient manner, such that the animal's absorption of the nutrients from animal feeds can be improved.

However, pH value of an animal's gastrointestinal tract (GIT) in different sections varies significantly. Taking meat-type poultry as an example, as widely known in the poultry industry, the pH value in a chicken's GIT varies between different sections of the GIT. In particular, the pH value of proventriculus and gizzard of the chicken GIT is around 1.1-3.2, while the pH value of duodenum and jejunum of the chicken GIT is around 5.5-6.6. As such, when the enzymes added into the poultry feed pass through the proventriculus and gizzard of the chicken GIT before they enter into the duodenum and jejunum, the enzymes' bioactivity and enzymatic efficiency can be significantly impaired or reduced due to the low pH environment in the proventriculus and gizzard. Other meat-type poultries have similar GIT environment variations, and therefore have same enzymes' bioactivity and efficiency problems as well.

Therefore, there is a long-existing need for a formula and/or method to preserve the bioactivity and enzymatic efficiency of the additive/supplement enzymes added to the poultry feed so as to enhance the FCR in the poultry and other meat-type animal industry.

SUMMARY OF THE INVENTION

One of the objectives of the invention is to provide a method for enhancing the FCR of the poultry feed in the poultry and other feed animal industry. The FCR of the poultry feed is enhanced by improving the bioactivity and enzymatic efficiency of the enzymes added to the poultry feed as addictive and/or supplement. To improve the bioactivity and enzymatic efficiency of the enzyme added to the poultry feed, in one embodiment of the invention, the mobile enzyme sequestration platforms are used to protect the enzyme in an adverse environment, e.g., low pH value, simulating certain sections of a living animal's GIT.

In one aspect, the invention relates to a method for enhancing the enzymatic efficiency of one or more enzymes added to poultry feed for a living subject. In one embodiment, the method includes: adding a cellulose-degrading enzyme to a mobile enzyme sequestration platform (MESP) so as to form an enzyme-MESP complex, adding the enzyme-MESP complex to poultry feed for a living subject, the enzyme efficiency of the cellulose-degrading enzyme of the enzyme-MESP complex after being exposed to a first adverse environment for a first period of time is at least 50% higher than the enzyme efficacy of the cellulose-degrading enzyme independent of the MESP being exposed to the first adverse environment for the first period of time.

In one embodiment, the first adverse environment has a pH value below 2.

In one embodiment, the first adverse environment has a pH value about 1.6.

In one embodiment, the first period of time is at least 30 minutes.

In one embodiment, the first adverse environment simulates the environment of the proventriculus and gizzard of a chicken's GIT.

In one embodiment, the first period of time simulates the time duration of poultry feed and enzyme-MESP complex remains in the proventriculus and gizzard of a chicken's GIT.

In another aspect of the invention, the enzyme efficiency of the cellulose-degrading enzyme of the enzyme-MESP complex after being exposed to a second adverse environment for a second period of time following the first period of time is at least 50% higher than the enzyme efficacy of the cellulose-degrading enzyme independent of the MESP being exposed to the second adverse environment for the second period of time following the first adverse environment for the first period of time.

In one embodiment, the second adverse environment has a pH value between 5.5-6.6.

In one embodiment, the second period of time is about 87 minutes.

In one embodiment, the second adverse environment simulates the environment of the duodenum and jejunum of a chicken's GIT; the second period of time simulates the time duration of poultry feed and enzyme-MESP complex remains in the duodenum and jejunum of a chicken's GIT.

In one embodiment, the cellulose-degrading enzyme is Xylanase.

In yet another aspect, the present invention provides a poultry feed for living subject improving feed-conversion-ratio. The poultry feed includes a mobile enzyme sequestration platform, a cellulose-degrading enzyme bound to the mobile enzyme sequestration platform so as to form an enzyme-MESP complex, a feed substrate containing lignocellulose for feeding a living subject, after the poultry feed being ingested by the living subject, the enzyme efficiency of the cellulose-degrading enzyme of the enzyme-MESP complex after being exposed to a first adverse environment for a first period of time is at least 50% higher than the enzyme efficacy of the cellulose-degrading enzyme independent of the MESP being exposed to the first adverse environment for the first period of time.

According to the invention, the method and the poultry feed system significantly enhance the FCR by improving the enzymatic efficiency of the enzymes added to the poultry feed as addictive and/or supplement. The advantage is that the enzymatic efficiency of the enzymes are protected when the enzymes pass through the section of the animal's GIT having an adverse environment such like low pH value.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. The same reference numbers may be used throughout the drawings to refer to the same or like elements in the embodiments.

DETAILED DESCRIPTION OF THE INVENTION

Figure 1:
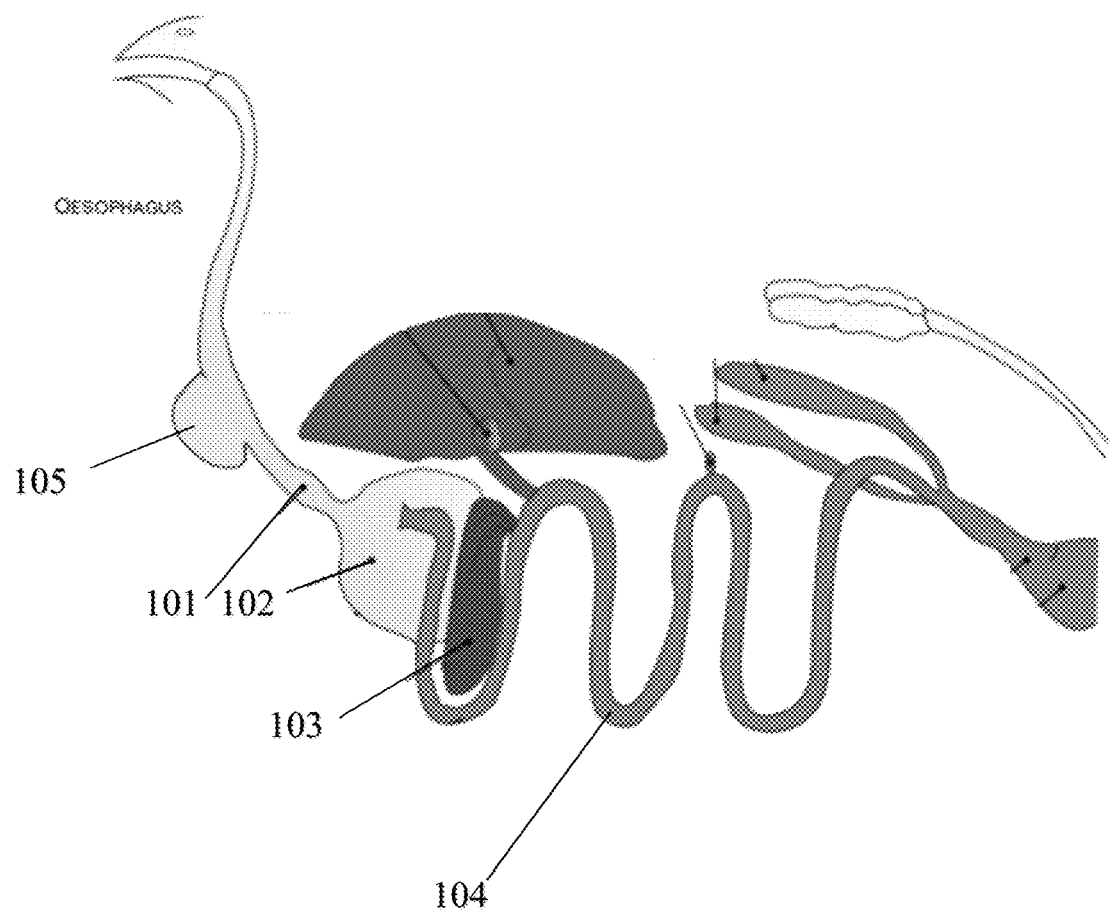
FIG. 1 shows schematically a diagram of a chicken's GIT, including the total time in residence for food bolus and pH value of each section of the GIT.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

It will be further understood that the terms "comprises" and/or "comprising," or "includes" and/or "including" or "has" and/or "having", or "carry" and/or "carrying," or "contain" and/or "containing," or "involve" and/or "involving", and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present invention, and will not be interpreted in an idealized or overly formal sense unless expressly so defined herein.

As used herein, the phrase at least one of A, B, and C should be construed to mean a logical (A or B or C), using a non-exclusive logical OR. As used herein, the term "and/or" includes any and all combinations of one or more of the associated listed items.

As used herein, the term "Feed Conversion Ratio (FCR)" is a measure of an animal's efficiency in converting feed mass into increases of the desired output. Specifically FCR is calculated as feed intake divided by weight gain, all over a specified period. Improvement in FCR means reduction of the FCR value. A FCR improvement of 2% means that the FCR was reduced by 2%.

As used herein, the term "meat-type poultry" refers to any avian species that is produced or used for meat consumption as understood by one skilled in the art. Examples of such avian species include, but are not limited to, chickens, turkeys, ducks, geese, quail, pheasant, ratites, and the like.

As used herein, the term "poultry feed" refers to a diet that can be administered to a member of the avian species to promote and maintain growth of the bird. A poultry feed can contain sources of protein, vitamins, minerals, energy such as fat, carbohydrates, and additional protein, antibiotics, and other substances or compounds known to be included in animal feeds.

As used herein, the terms "growth" or "growth performance" refer to increases in either, or both, weight and size (e.g., height, width, diameter, circumference, etc.) over that which would otherwise occur without implementation of the methods and/or administration of the compositions of the present invention. Growth can refer to an increase in the mass (e.g., weight or size) of the entire animal or of a particular tissue (e.g., muscle tissue in general or a specific muscle). Alternatively, growth can indicate a relative increase in the mass of one tissue in relation to another, in particular, an increase in muscle tissue relative to other tissues (e.g., adipose tissue). Growth further relates to nutritional status and disease resistance wherein improvement of nutritional status and/or increase in disease resistance is also indicative of improved growth performance.

As used herein, the term "Xylanase" means any of a class of enzymes that degrade the linear polysaccharide xylan into xylose, and thus breaking down hemicellulose. Xylanase may include 1,4-beta-D-xylan-xylohydrolase, and endoxylanase (E.C.3.2.1.8), β-xylosidase (E.C.3.2.1.37), α-glucuronidase (E.C.3.2.1.139), α-arabinofuranosidase (E.C.3.2.1.55) and acetylxylan esterase (E.C.3.1.1.72).

As used herein, the term "Phytase" means any type of phosphatase enzyme that catalyzes the hydrolysis of phytic acid. Phytase may include histidine acid phosphatases (HAPS), beta-propeller phytases (BPPs), purple acid phosphatases (PAPs), and protein tyrosine phosphatase-like phytases (PTP-like phytases).

As used herein, the term "Xylanase activity" means the hydrolysis of xylan into smaller molecules.

As used herein, the term "Phytase activity" means the hydrolysis of phytate (myo-inositol hexakisphosphate) to (1) myo-inositol and/or (2) mono-, di-, tri-, tetra- and/or penta-phosphates thereof and (3) inorganic phosphate.

As used herein, the terms "enzyme variant" means a polypeptide having enzyme activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

As used herein, the term platform may refer to, be part of, or include a mobile enzyme sequestration platform (MESP).

Even though Xylanase and Phytase are being used as two examples of the enzymes which are used as poultry feeds additives and enzyme bonded to and protected by the MESP, the present invention is also application to other enzymes commonly used as additives for the poultry feed.

Even though chicken is used as an embodiment of the present invention, the present invention is also applicable to other avian species and other living animals in the poultry and herd industries, including but not limited to turkey, ducks, pigs, beef cows, milk cows, goats, sheep, and etc.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The livestock (e.g. poultry) industry has interests in developing feed and feed supplements that allow for optimal absorption of nutrients in animal GIT so as to improving the growth performance by optimizing FCR. Optimizing FCR results in growing an animal of a target weight with less feed. In short, enhancing FCR allows the growth of animal biomass to a target weight using less gram weight of feed.

It is a common practice for the poultry industry to include additives and/or supplements, such as enzymes, to the poultry feed containing lignocellulose. The enzymes are designed to assist breakdown of poultry feeds and thereby facilitate absorption of poultry feed components (i.e., protein, lipids, carbohydrates).

However, currently used enzymes do not result in a significant enhancement of FCR due to the pH variation in different sections of the GIT of a poultry, such like a chicken. In particular, a chicken GIT has the proventriculus and gizzard where has ultra-low pH regions (e.g., pH 1.6). Downstream of the proventriculus and gizzard is the duodenum and jejunum having a higher pH regions of the GIT (e.g., pH 5.5) where nutrients are absorbed and where the enzymes need to be optimally active to breakdown the various components of the feed (e.g., lipids, proteins, carbohydrate). Hence, the added enzymes, ingested along with the poultry feed, lose their bioactivity in the ultra low pH region (proventriculus and gizzard) before reaching a higher pH regions (duodenum and jejunum), where the enzymes are expected to enhance the breaking down the poultry feed.

As such, preserving and improving the enzyme efficiency of additives and/or supplements in the poultry feeds and other animal feed is essential for enhancing the FCR. Hence, methods to optimize enzymatic efficiency and synergy in multi-enzyme systems are 'hot topics' in academic and industry research and development.

Instead of focusing on modifying enzymes for inherent enhancement of structural stability and function under adverse environment in the animal's GIT, the present invention has opted to design and develop a protein platforms to which enzymes may be bound.

These platforms are engineered from chaperone proteins found in hyperthermophilic archaea which inhabits in volcanic hot springs and other geothermal places with temperature exceeding 85 Celsius degrees and pH value as low as 1. These chaperone proteins form complexes to protect other proteins within the cell under 'extreme' conditions (e.g., high temperature fluxes and pH fluxes). As disclosed herein, the present invention uses a novel protein complex called a mobile enzyme sequestration platform (MESP) comprising these thermophilic proteins. The MESP binds to an enzyme of interest (e.g. Xylanase and Phytase) and protects the enzymes of interest when the enzyme of interest passing through the low pH environments, such as the proventriculus and gizzard region of a chicken's GIT, and therefore enhances the bioactivity and efficiency of enzyme added to the poultry feed.

FIG. 1 schematically shows a GIT of a chicken, the pH value in different sections of the chicken's GIT, as well as the duration of the ingested food and enzyme remain in each different section. As reflected in FIG. 1, after ingested by a chicken, the poultry feed and enzyme firstly enter into the crop 105 having a pH value between 4.3-5.9 and would remain in the section for up to about 12 minutes. Therefrom the poultry feed and enzyme travel into the proventriculus 101 and gizzard 102 section, having a pH value between 1.1-3.2 and would remain there for up to about 37 minutes. It should be noted that the pH value of the proventriculus 101 and gizzard 102 creates an adverse acidic environment, which denatures a significant number of enzymes, e.g. Xylanase and Phytase. As a result, these enzymes lose their bioactivity and enzymatic efficiency by passing through this section if no other protective measure is taken.

After leaving the proventriculus 101 and gizzard 102, the poultry feed and enzyme enter into the duodenum 103 and jejunum 104 section, where the poultry feed are broken down into components and absorbed within a period of approximately 87 minutes. Therefore, ideally, the enzyme as addictive and/or supplement aiming at improving the FCR should maintain its enzymatic efficiency when they reach the duodenum 103 and jejunum 104 section. In order to achieve this, the enzyme such like Xylanase must be protected when it passes through the low pH acidic environment of the proventriculus 101 and gizzard 102 locating upstream of the duodenum 103 and jejunum 104 section.

The present invention protects the enzyme from the adverse environment by bolstering the enzymatic hydrolysis via the use of platforms. Cellulose degrading microorganisms, such as bacteria and fungi, employ expansive protein "scaffolds" to degrade cellulosic biomass. These large protein complexes are referred to as cellulosomes. Synthesized artificial cellulosomes have evolved into protein platforms that only vaguely resemble natural cellulosomes.

Indeed, platform technology can have several forms. Immobilized platforms bind lignocellulose deconstruction enzymes to columns or other surfaces that allow slurry to pass through or over an enzyme array, while the present invention uses a mobile platform that could bind enzymes and still move through slurry as a large protein complex. With respect to the MESP in the present invention, at the core of the platform is an altered double-nonameric ring (18-mer) heat shock protein complex derived from a hyperthermophilic archeaon of the genus *Sulfolobus* (see FIGS. 2A-C). The subunits of the complex were modified to bind cellulosome enzymes of the cellulose-degrading bacteria *Clostridium thermocellum*.

Figure 2A:
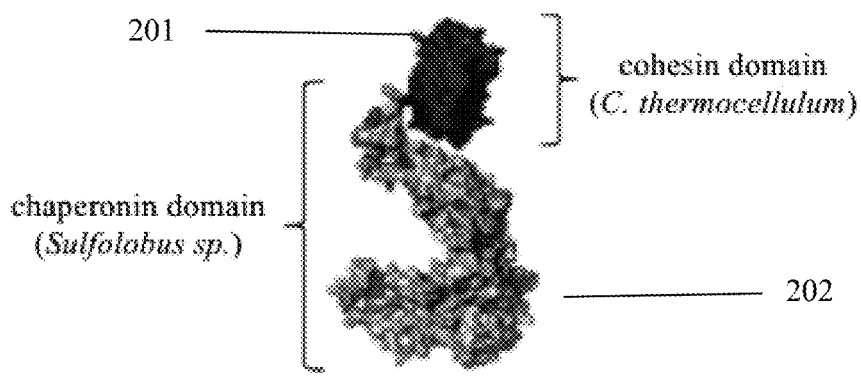
FIG. 2A shows schematically a Pymol model of a Heat Shock Protein-coh fusion protein (HSP-coh).

FIG. 2A shows a subunit of Pymol model of HSP-coh fusion protein. Circular permutant of a group II chaperonin "heat-shock" protein (grey) 202 from archaeon *Sulfolobus* sp. (lab strain) is linked to cohesin (Type 1) protein (black) 201 from bacterium *Clostridium thermocellum*.

Figure 2B:
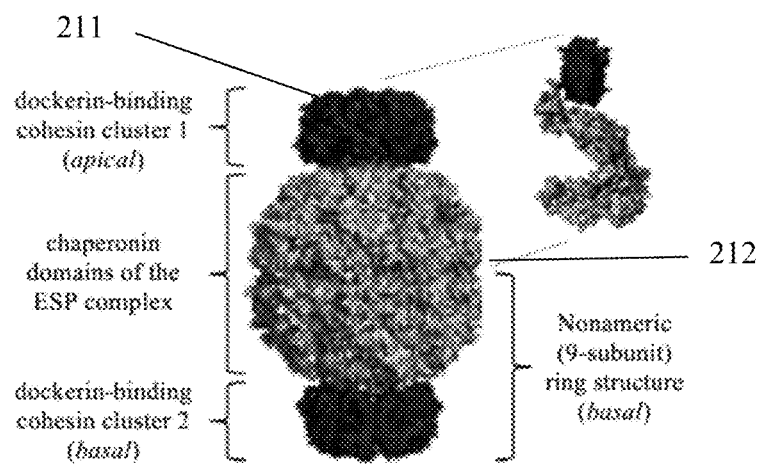
FIG. 2B shows schematically a Pymol model of an uncharged MESP complex comprising HSP.

FIG. 2B shows an uncharged Pymol model of MESP complex. In one embodiment, nine HSP-coh subunits constitute 18-mer ESP having a two-ring structure. Cohesin (type 1) domains from each subunit cluster at apical and basal extremities of the MESP complex and are capable of binding enzymes equipped with a dockerin (type 1) domain 211. The chaperonin domain of subunits forms the central part 212 of the MESP. This model illustrates an "uncharged" configuration of the MESP, which has not bound any enzyme.

Figure 2C:
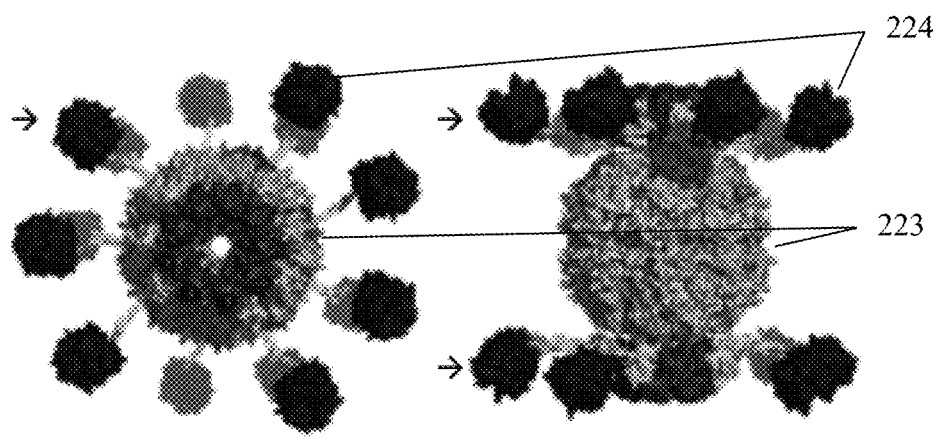
FIG. 2C shows a Pymol model of an enzyme-charged MESP complex.

FIG. 2C shows a Pymol model of enzyme-charged MESP complex. Top view of an MESP complex 223 with dockerin-containing enzymes 224 bound in on the left. Side view of an ESP complex showing enzyme binding (arrows) at apical and basal cohesin clusters is on the right. In one embodiment, one or more enzyme bind to the dockerin-binding cohesion cluster.

Figure 2D:
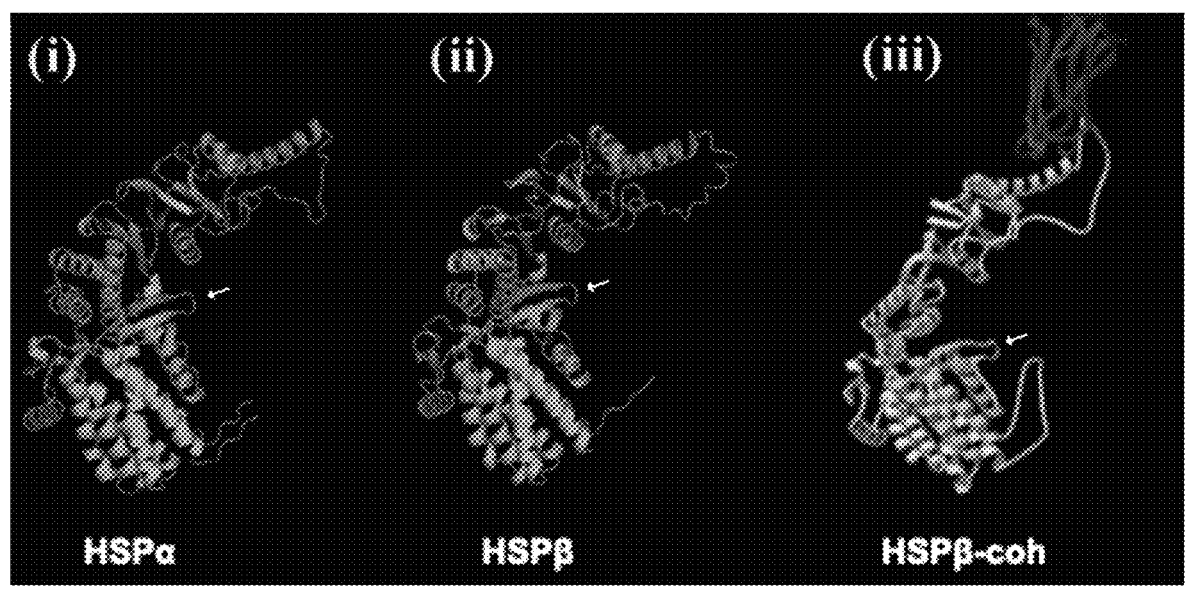
FIG. 2D shows structural models of HSPα, HSPβ, and HSPβ-coh subunits.

FIG. 2D(i) shows a 3-D structure model of the HSPα subunit; FIG. 2D(ii) shows a 3-D structure model of the HSPβ subunit; and FIG. 2D(iii) shows a 3-D structure model of engineered/fused HSPβ-coh. In one embodiment, the HSPα is generated from *Sulfolobus* isolate. In one embodiment, the HSPβ, which is fused with cohesion and forms the HSPβ-coh, is generated from *S. shibatae*.

In one embodiment, a MESP is a homomer and comprises only HSPα subunits. In one embodiment, a MESP is a homomer and comprises only HSPβ-coh subunits. In one embodiment, a MESP is a heteromer and comprises both HSPα subunits and HSPβ-coh subunits. In one embodiment, the heteromer MESP comprises HSPα subunits and HSPβ-coh subunits which are arranged in a manner to space out the dockerin binding locations on each subunit. This arrangement pattern effectively reduce the steric interference between adjacent bound enzymes on MESP when MESP is charged.

In one embodiment, the amount of enzyme binds to the apical cohesin cluster equals to the amount of the enzyme binds to the basal cohesin cluster. In another embodiment, the amount of enzyme binds to the apical cohesin cluster is different from the amount of the enzyme binds to the basal cohesin cluster. In one embodiment, there is only one type of enzyme binding to the apical and basal cohesin clusters of the MESP. In one embodiment, there is more than one type of enzymes binding to the apical and basal cohesin clusters of the MESP.

In one embodiment, Xylanase with a dockerin region binds to the dockerin-binding cohesin cluster of MESP complex. In another embodiment, a commercially available Phytase with a dockrin region binds to the dockerin binding cohesion cluster of MESP complex. In yet another embodiment, an *E. coli* derived phytase with a dockrin region binds to the dockerin binding cohesion cluster of MESP complex.

MESP Construction

The fusion protein was constructed using recombinant DNA methods. This fusion protein, HSPβ-coh (FIG. 2A) is composed of a circular permutant of HSPβ, an archaeon (*Sulfolobus* sp.) heat-shock protein, and the cohesin module of CipA from the bacterium *Clostridium thermocellum* (residues 179-325; NCBI Q06851). This fusion construct contains a nine (9) amino acid linker (i.e., GGSGGSGGS) between the HSPβ and cohesin domains. The DNA encoding the HSPβ-coh fusion construct was inserted into a pET19b expression vector from Novagen®. For storage the plasmid was transformed into DH5a cells from Invitrogen®. For overexpression of the fusion protein, the pET19b-HSPβ-coh plasmid was transformed into another line of bacteria (*E. coli*)—namely, BL21 CodonPlus (DE3) RIL cells from Stratagene®. In the same manner, PCR-amplified genes for several cellulases (and other lignocellulose deconstruction enzymes) expressed by *C. thermocellum* (ATCC27405DTM) were stored and expressed.

Protein Purification and Gel Electrophoresis

Overexpressed proteins including the HSPβ-coh fusion protein and *C. thermocellum* enzymes were purified using a Fast Perfusion Liquid Chromatography (FPLC) system from Pharmacia/GE Amersham®. A Superdex 200 size exclusion column and a Mono Q ion exchange column from GE Healthcare® were used to purify desired proteins from lysate. SDS-PAGE and western blot analysis were performed in initial rounds of expression to confirm the purity of protein suspensions and validate molecular weight.

MESP Complex Formation

To induce complex formation of 18 HSP-coh fusion proteins to form an 18-mer double ring enzyme sequestration platform (ESP), mixtures of the fusion proteins at 2 mg/ml were incubated with 1 mM ATP and 50 mM Mg2+ at 4° C. for 8-12 hr. Complex formation was confirmed using electron microscopy.

Transmission Electron Microscopy

Approximately 5 µl of protein suspension was spotted onto a formvar-coated copper grid and incubated for 10 min in a humidity chamber. The grid was rinsed with distilled water and negatively stained with 2% (w/v) uranyl acetate for 2 min. The stain was wicked off and the sample was air-dried. Grids were imaged in a Hitachi H-7100 TEM at 75 kV. Images were captured at 60,000-150,000× magnification.

MESP Charging with Enzyme

To charge the ESP with enzymes, 7.72 uM ESP complexes were incubated at room temperature for 15 min. with 6.86 uM enzyme or enzyme cocktail in the presence of 0.7 mM ATP, 17.4 mM MgCl2, and 5 mM CaCl2 in 22.2 µl of a 50 mM Tris-maleate buffer (pH 6.0). In one embodiment, Xylanase is used as the enzyme charging the MESP.

Enzyme Activity Assay for Xylanase and Xylanase-MESP Complex

Enzyme activity was measured in four separate groups simulating chicken GIT's environment.

TABLE I

Agents added to each group in simulated chicken GIT assay

| | MESP | Xylanase | Poultry feed |
|---|---|---|---|
| Group I | No | No | Yes |
| Group II | Yes | No | Yes |
| Group III | No | Yes | Yes |
| Group IV | Yes | Yes | Yes |

In each group, the MESP and/or Xylanase together with poultry feed are suspended in a 50 µl reaction solution containing: 20 mM Tris-maleate (pH 6.0), 1 mM ATP, 25 mM MgCl2, and, 1 mM CaCl2. Each group undergoes a first stage of a 37 minutes exposure to a pH value of 1.6, simulating food bolus in the proventriculus and gizzard, followed by a second stage of 87 minutes exposure to a pH value between 5.5-6.6, simulating food bolus in the duodenum and jejunum, where the enzyme should break down the ingested poultry feed actively.

A colorimetric assay to assess sugar reduction efficiency is conducted thereafter.

The colorimetric assay compares hydrolytic efficiency between free Xylanase, free MESP, and MESP-bound Xylanase. After the reaction, samples in each group were separately centrifuged at 3000 RPM for 10 minutes to remove residual particles of the pretreated biomass and diluted 10-fold in sterile DI water. Afterwards, 30 µl of the dilute sample was mixed with 30 µl of a 50 mM Na2CO3/10 mM KCl solution and 30 µl of a 1.5 mM $K_3Fe(CN)_6$ solution. This 90 µl mixture was heated for 15 min at 99° C. and then transferred to a well in a 96-well plate (or a 0.5 ml microcentrifuge tube) containing 150 ml of a 0.15% $NH_4Fe(SO_4)_2 \cdot 12\ H_2O$ and 0.1% SDS/0.05N $H_2SO_4$. After incubation at room temperature for 15 min. OD650 nm readings were taken using a SpectraMAX M2e automated plate reader (or a Nanodrop spectrophotometer).

Figure 3:
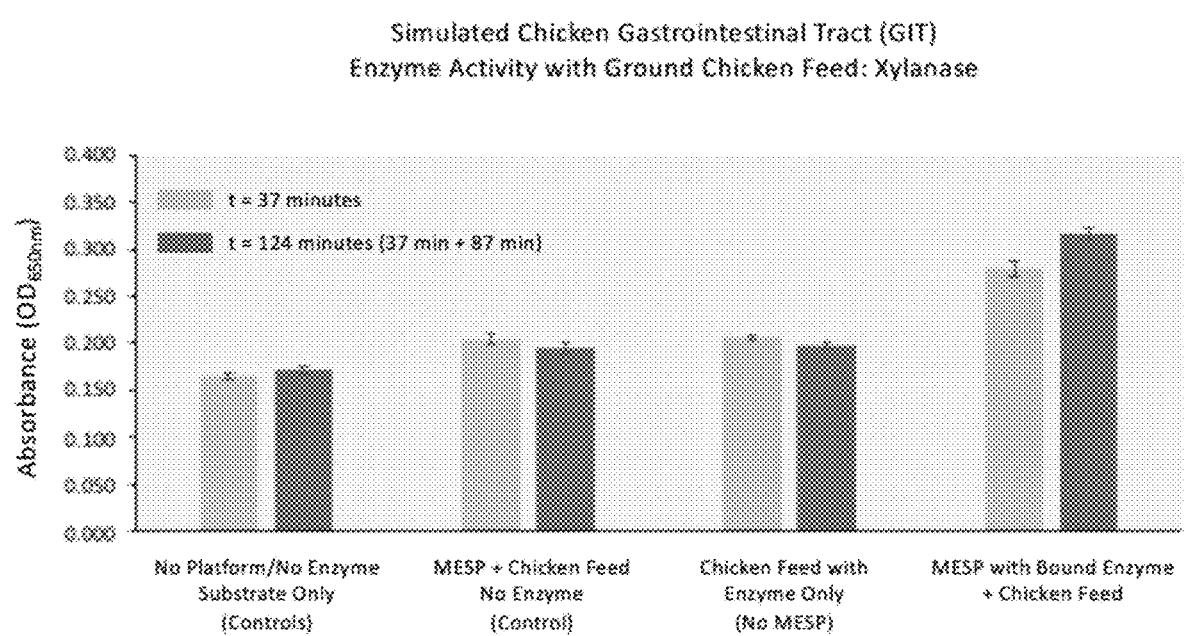
FIG. 3 shows Xylanase enzyme activity and Xylanase-MESP complex enzyme activity with ground chicken poultry feed in an environment simulating a chicken's GIT.

FIG. 3 shows results of the colorimetric assay of Xylanase enzyme activity and Xylanase-MESP complex enzyme activity with ground chicken poultry feed in an environment simulating a chicken's GIT. The results for group I, II, III, and IV are presented from left to right on X axis, and the absorbance readings at OD650 nm are presented by Y axis. For each group, the left column represents the OD650 nm readings after stage I of appx. 37 minutes exposure to pH value about 1.6, while the right column represents the OD650 nm readings after stage II of appx. 87 minutes exposure to pH value about 5.5-6.6.

In group I which only poultry feed substrate is added without the MESP and Xylanase, the absorbance at OD 650 nm is 0.150 after stage I of 37 minutes exposure to pH 1.6, and the absorbance at OD 650 nm is no significantly higher than 0.150 after stage II of 87 minutes exposure to pH 5.5-6.6.

In group II and III, MESP and Xylanase are added to the poultry feed substrate independent of each other. In both group, the absorbance at OD 650 nm after stage I of 37 minutes exposure to pH 1.6 and the absorbance at OD 650 nm after stage II of 87 minutes exposure to pH 5.5-6.6 are similar to each other and are both slightly below 0.200. The OD 650 nm after stage II is lower than the OD 650 nm after stage I in both group II and III, respectively.

However, in sharp contrast to the group I, II and III, group IV has MESP bound with Xylanase added into the poultry diet. After exposure to pH 1.6 for 37 minutes, the absorbance at OD 650 nm is between 0.250-0.300, which is significantly higher than the 0.150-0.200 reading when either MESP or Xylanase was added into the poultry feed alone. Following the stage I, the food bolus was incubated in an environment having a pH between 5.5-6.6 for 87 minutes before the absorbance at OD 650 nm are tested and read again. The absorbance at OD 650 nm of group IV after the stage II is above 0.300, which is nearly as twice as the absorbance reading at OD 650 nm of Group I, II and III. This clearly shows that the enzymatic efficiency of Xylanase is approximately at least doubled when it is bounded with MESP.

This leads to the conclusion that MESP is effective in protecting the enzymatic efficiency of Xylanase in an adverse environment which would denature the enzyme. The MESP protects enzyme supplements added to the poultry feed when the MESP-enzyme complex passes through the low pH sections of the chicken GIT, so as to permit the enzyme reach to the nutrient absorption section of the GIT without losing its enzymatic efficiency. Therefore, MESP enhances the FCR by increasing the bioactivity and enzymatic efficiency of the enzyme supplements.

Enzyme Activity Assay for Commercial Phytase and Phytase-MESP Complex

Figure 4A:
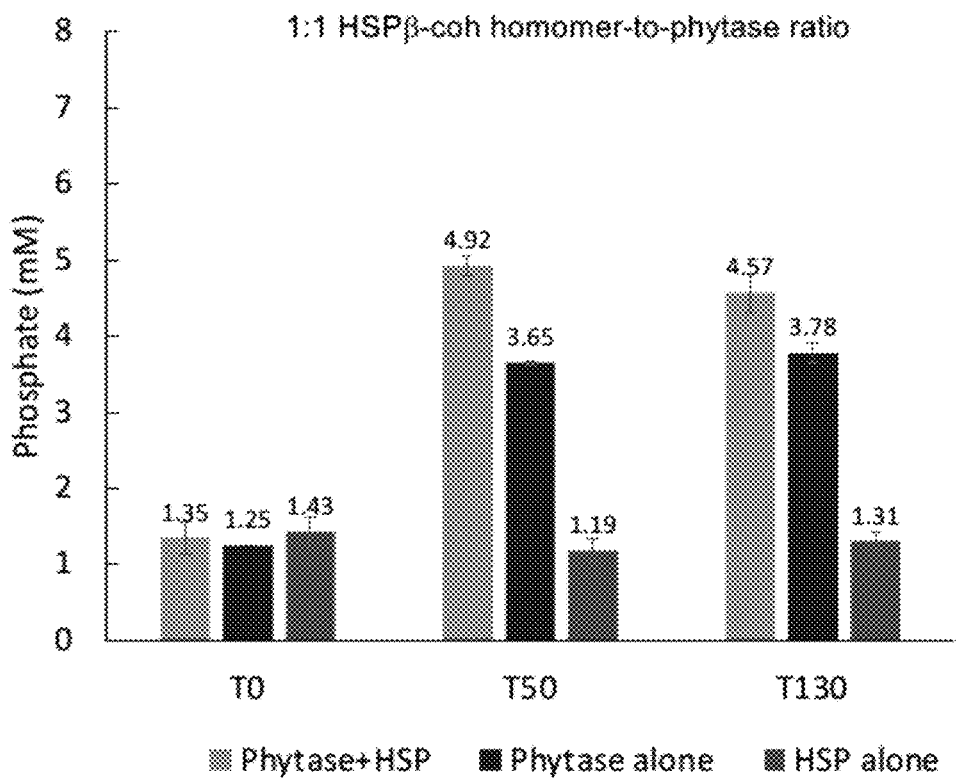
FIG. 4A-B shows Phytase enzyme activity and Phytase-MESP with ground chicken poultry feed in an environment simulating a chicken's GIT.
Figure 4B:
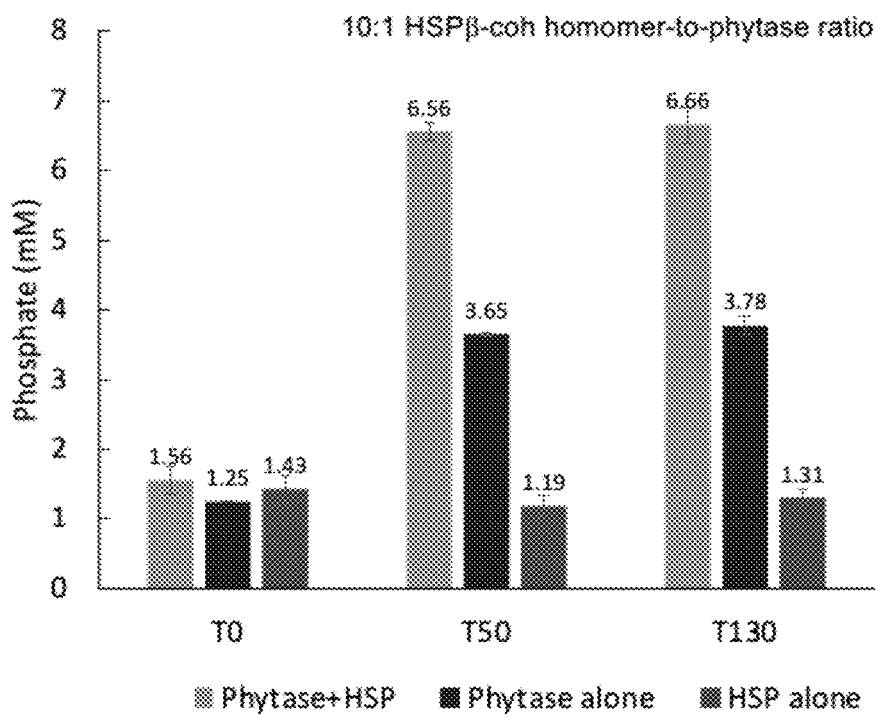

FIG. 4A-B shows results of enzyme activity assay of Phytase and Phytase-MESP complex enzyme activity with ground chicken poultry feed in an environment simulating a chicken's GIT.

In one embodiment, the MESP being used in this embodiment is HSPβ-coh homomer. In another embodiment, the MESP being used is HSPα-coh and HSPβ-coh heteromer. Phytase is commercially available Phytase.

Enzyme activities of Phytase alone, HSPβ-coh homomer as MESP alone, and Phytase together with HSPβ-coh homomer are measured by amount of phosphate, which is produced via hydrolysis of phytate by the phytase. That is, at any stage, the more phosphate detected, the higher the Phytase bioactivity is. The phosphate was measured at three different stage: TO which is before the Phytase, HSP or Phytase-HSP undergoes low pH 1.1-3.2, T50 which is after the Phytase, HSP or Phytase-HSP undergoes low pH 1.1-3.2 treatment for about 37 minutes, but before the Phytase, HSP or Phytase-HSP undergoes high pH 5.5-6.6 treatment, and T130 which is after the Phytase, HSP or Phytase-HSP undergoes high pH 5.5-6.6 treatment for about 60-100 minutes. Low pH 1.6-3.2 simulates the environment of the proventriculus and gizzard of the chicken GIT, 37 minute duration simulates the time duration the food bolus remains in the proventriculus and gizzard. High pH 5.5-6.5 simulates the environment in the duodenum and jejunum of GIT, and 60-100 minute duration simulates the time duration that the food bolus remains in the duodenum and jejunum. All assays are carried out under a temperature of 40° C., which simulates the body temperature of a chicken.

In one embodiment, the method for MESP construction, protein purification and gel electrophoresis for HSPβ-homomer protein, MESP complex formation, and transmission electron microscopy are the same as described above for the Xylanase. While the step of MESP charging with enzyme is same as that for Xylanase essay, the enzyme being used is Phytase. It should be known that Xylanase and Phytase were only used as examples, the method is also applicable to other enzymes used for facilitating the breaking down of cellulose and other nutrients in the poultry feeds.

Enzyme Activity Assay for Phytase and Phytase-MESP Complex

In each group, the MESP, Phytase, or Phytase-MESP together with poultry feed are suspended in a 50 µl reaction solution containing: 20 mM Tris-maleate (pH 6.0), 1 mM ATP, 25 mM MgCl2, and, 1 mM CaCl2.

FIG. 4A illustrates the enzyme activity when the ratio of HSPβ-coh homomer as MESP and Phytase is 1:1, while FIG. 4B illustrates the enzyme activity when the ratio of HSPβ-coh homomer as MESP and Phytase is 10:1.

At time point TO, that is before the Phytase-HSP, Phytase, or HSP undergoes the low pH 2, the phosphate measured in the assay using Phytase-HSP (left column) is 1.35 mM, the phosphate measured in the assay using Phytase alone (mid column) is 1.25 mM, and the phosphate measured in the assay using HSP alone (right column) is 1.43 mM.

At time point T50, that is after the Phytase-HSP, Phytase, or HSP undergoes the low pH 2 for a time duration about 37 minutes, the phosphate measured in the assay using Phytase-HSP (left column) is 4.92 mM, the phosphate measured in the assay using Phytase alone (mid column) is 3.65 mM, and the phosphate measured in the assay using HSP alone (right column) is 1.19 mM.

At time point T130, that is after the Phytase-HSP, Phytase, or HSP undergoes the high pH 5.5-6.6 for a time duration about 60-100 minutes, the phosphate measured in the assay using Phytase-HSP (left column) is 4.57 mM, the phosphate measured in the assay using Phytase alone (mid column) is 3.78 mM, and the phosphate measured in the assay using HSP alone (right column) is 1.31 mM.

Therefore, it is clear to one having ordinary skill in the art that, after 37 minutes low pH treatment, the enzyme activity of Phytase-HSP 4.92 is obviously higher than the enzyme activity of Phytase alone 3.65. After 60-100 minutes high pH treatment, the enzyme activity of Phytase-HSP 4.57 is still obviously higher than the enzyme activity of Phytase alone 3.78.

This advantage of Phytase-HSP's enzyme activity is more significant when the ratio of HSPβ-coh homomer to Phytase is 10:1, as illustrated in FIG. 4B, In particular, at time point TO, that is before the Phytase-HSP, Phytase, or HSP undergoes the low pH 2, the enzyme activity of Phytase-HSP, Phytase, or HSP are not significantly different from that their enzyme activity when the ratio of HSPβ-coh homomer to Phytase is 1:1.

However, the enzyme activity of Phytase-HSP when the ratio is 10:1 increases significantly as compared to the enzyme activity of Phytase-HSP when the ratio is 1:1.

At time point T50, that is after the Phytase-HSP, Phytase, or HSP undergoes the low pH 2 for a time duration about 37 minutes, the phosphate measured in the assay using Phytase-HSP (left column) is 6.56 mM, the phosphate measured in the assay using Phytase alone (mid column) is 3.65 mM, and the phosphate measured in the assay using HSP alone (right column) is 1.19 mM.

At time point T130, that is after the Phytase-HSP, Phytase, or HSP undergoes the high pH 5.5-6.6 for a time duration about 60-100 minutes, the phosphate measured in the assay using Phytase-HSP (left column) is 6.66 mM, the phosphate measured in the assay using Phytase alone (mid column) is 3.78 mM, and the phosphate measured in the assay using HSP alone (right column) is 1.31 mM.

As such, there is as much as 80% increase in enzyme activity when the phytase is bound to HSP as MESP.

Figure 5A:
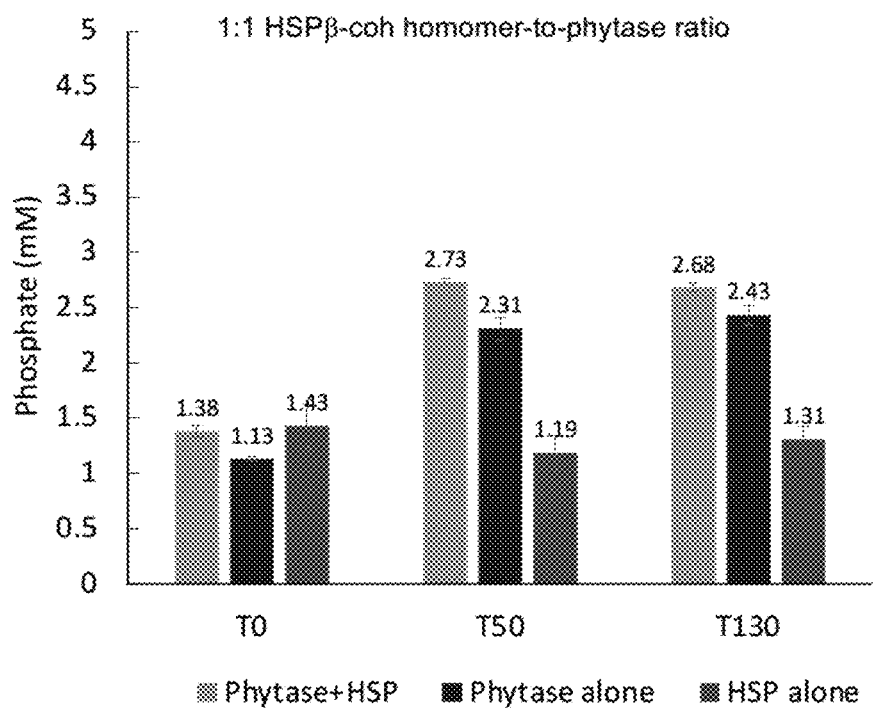
FIG. 5A-B shows E. coli derived Phytase activity and E. coli derived Phytase-MESP activity with ground chicken poultry feed in an environment simulating a chicken's GIT.
Figure 5B:
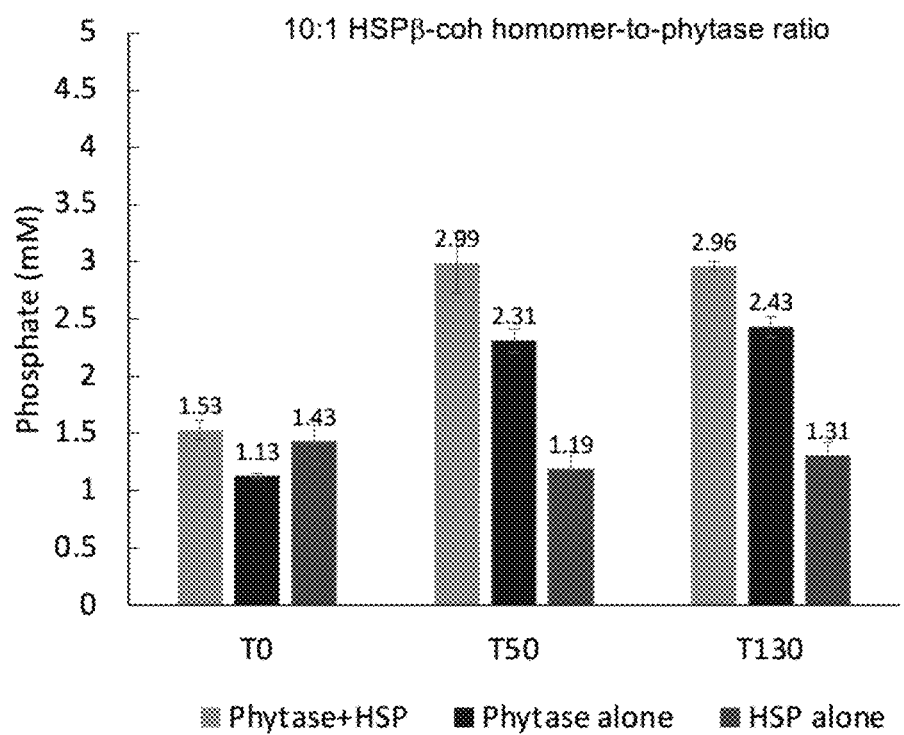

FIG. 5A-B shows *E. coli.* derived Phytase activity and *E. coli* derived Phytase-MESP activity with ground chicken poultry feed in an environment simulating a chicken's GIT.

The *E. coli.* derived Phytase-dockerin protein, which bonds to the MESP, is produced by plasmid pET-19b comprising a nucleic acid sequence having a SEQ ID No: 1, via methods well known and commonly understood in the industry. The nucleic acid sequence comprises pET-19b vector sequence, a phytase encoding sequence and a dockerin encoding sequence, and a linker sequence between the phytase encoding sequence and dockerin encoding sequence. The *E. coli.* derived Phytase-dockerin comprises an amino acid sequence of SEQ ID No: 2. The amino acid sequence comprising a phytase domain, a dockerin domain, and a linker domain between the phytase domain and dockerin domain. In one embodiment, the linker is a linker having an amino acid sequence of SEQ ID NO: 3. It should be noted in other embodiments, other linkers can be used. In one embodiment, a linker has an amino acid sequence of SEQ ID NO: 4. This linker having SEQ ID No: 4 improves enzyme reactivity bound onto the MESP by separating enzymes spatially.

The phytase encoding sequence are derived from sources including Aspergillus niger, Bacillus subtilis, Bacillus licheniformis, Citrobacter braakii, Escherichia coli, Obesumbacterium proteus, Raoultella terrigena, Shigella sp. CD2.

The method for analyzing enzyme activity of the E. coli. derived Phytase is the same as to the method described above for analyzing enzyme activity of commercial Phytase. FIG. 5A illustrates the enzyme activity of the E. coli. derived Phytase-MESP (HSP)-, E. coli. derived Phytase alone, and MESP (HSP) alone, when the ratio of HSPβ-coh homomer to the Phytase is 1:1. The enzyme activity of Phytase-HSP (Phosphate is 2.73 mM) is higher than the enzyme activity of Phytase alone (Phosphate is 2.31 mM), after a 37-minutes low pH treatment. After a 60-100 minutes high pH 5.5-6.6 treatment, the enzyme activity of Phytase-HSP (Phosphate is 2.68 mM) is also higher than the enzyme activity of Phytase alone (Phosphate is 2.43 mM).

When the ratio of HSPβ-coh homomer to the Phytase is 10:1, as illustrated in FIG. 5B, the MESP clearly enhances the enzyme activity more significantly. In one embodiment, the enzyme activity of Phytase-HSP (Phosphate is 2.99 mM) is higher than the enzyme activity of Phytase alone (Phosphate is 2.31 mM), after a 37-minutes low pH treatment. After a 60-100 minutes treatment in high pH between about 5.5-6.6, the enzyme activity of Phytase-HSP (Phosphate is 2.96 mM) is also higher than the enzyme activity of Phytase alone (Phosphate is 2.43 mM). As such, there is as much as 20-30% increase in the E. coli derived Phytase's enzyme activity when the E. coli derived phytase is bound to HSP as MESP and being added to the poultry feed.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

What is claimed is:

1. A method for enhancing the enzymatic efficiency of an enzyme added to poultry feed for a living subject, comprising:
   adding a cellulose-degrading enzyme to a mobile enzyme sequestration platform(MESP) so as to form an enzyme-MESP complex; and
   adding the enzyme-MESP complex to poultry feed for a meat-type poultry;
   wherein the enzyme efficiency of the cellulose-degrading enzyme of the enzyme-MESP complex after being exposed to a first adverse environment for a first period of time is at least 20% higher than the enzyme efficacy of the cellulose-degrading enzyme independent of the MESP after being exposed to the first adverse environment for the first period of time.

2. A method for enhancing the enzymatic efficiency of an enzyme added to poultry feed according to claim 1, wherein the first adverse environment has a pH value below 2.

3. A method for enhancing the enzymatic efficiency of an enzyme added to poultry feed according to claim 1, wherein the first adverse environment has a pH value about 1.6.

4. A method for enhancing the enzymatic efficiency of an enzyme added to poultry feed according to claim 1, wherein the first period of time is at least 30 minutes.

5. A method for enhancing the enzymatic efficiency of an enzyme added to poultry feed according to claim 1, wherein the first adverse environment simulates the environment of the proventriculus and gizzard of a chicken's GIT.

6. A method for enhancing the enzymatic efficiency of an enzyme added to poultry feed according to claim 1, wherein the first period of time simulates the time duration of poultry feed and enzyme-MESP complex remains in the proventriculus and gizzard of a chicken's GIT.

7. A method for enhancing the enzymatic efficiency of an enzyme added to poultry feed according to claim 1, wherein the enzyme efficiency of the cellulose-degrading enzyme of the enzyme-MESP complex after being exposed to a second adverse environment for a second period of time following the first period of time is at least 20% higher than the enzyme efficacy of the cellulose-degrading enzyme independent of the MESP after being exposed to the second adverse environment for the second period of time following the first adverse environment for the first period of time.

8. A method for enhancing the enzymatic efficiency of an enzyme added to poultry feed according to claim 7, wherein the second adverse environment has a pH value between 5.5-6.6.

9. A method for enhancing the enzymatic efficiency of an enzyme added to poultry feed according to claim 7, wherein the second period of time is about 87 minutes.

10. A method for enhancing the enzymatic efficiency of an enzyme added to poultry feed according to claim 7, wherein
    the second adverse environment simulates the environment of the duodenum and jejunum of a chicken's GIT;
    the second period of time simulates the time duration of poultry feed and enzyme-MESP complex remains in the duodenum and jejunum of a chicken's GIT.

11. A method for enhancing the enzymatic efficiency of an enzyme added to poultry feed according to claim 1, wherein the cellulose-degrading enzyme comprises at least one of Xylanase and Phytase.

12. A poultry feed for meat-type poultry improving feed-conversion-ratio, comprising:
    a mobile enzyme sequestration platform;
    a cellulose-degrading enzyme bound to the mobile enzyme sequestration platform so as to form an enzyme-MESP complex;
    a feed substrate containing lignocellulose for feeding a living subject;
    wherein after the poultry feed being ingested by the meat-type poultry, the enzyme efficiency of the cellulose-degrading enzyme of the enzyme-MESP complex after being exposed to a first adverse environment for a first period of time is at least 20% higher than the enzyme efficacy of the cellulose-degrading enzyme independent of the MESP being exposed to the first adverse environment for the first period of time.

13. A poultry feed for meat-type poultry improving feed-conversion-ratio according to claim 12, wherein the first adverse environment simulates the environment of the proventriculus and gizzard of a chicken's GIT.

14. A poultry feed for meat-type poultry improving feed-conversion-ratio according to claim 12, wherein the first period of time simulates the time duration of poultry feed and enzyme-MESP complex remains in the proventriculus and gizzard of a chicken's GIT.

15. A poultry feed for meat-type poultry improving feed-conversion-ratio according to claim 12, wherein the second adverse environment simulates the environment of the duodenum and jejunum of a chicken's GIT; the second period of time simulates the time duration of poultry feed and enzyme-MESP complex remains in the duodenum and jejunum of a chicken's GIT.

16. A poultry feed for meat-type poultry improving feed-conversion-ratio according to claim 12, wherein the cellulose-degrading enzyme comprises at least one of Xylanase and Phytase.

17. A poultry feed for meat-type poultry improving feed-conversion-ratio according to claim 12, wherein the MESP comprises at least one fusion protein composed of a heat shock protein from archaeon *Sulfolobus* sp. linked to a cohesion protein from bacterium *Clostridium thermocellum* via a linker protein.

18. A mobile enzyme sequestration platform(MESP), comprising:
at least one Heat Shock Protein(HSP)$\alpha$-cohesin fusion protein subunit, and
at least one HSP$\beta$-cohesin fusion protein subunit;
wherein the HSP$\alpha$-cohesin fusion protein subunit comprising a HSP$\alpha$ domain and a cohesion domain; the HSP$\beta$-cohesin fusion protein subunit comprising a HSP$\beta$ domain and a cohesion domain;
wherein the MESP is bounded to a cellulose-degrading enzyme.

* * * * *

SEQUENCE LISTING

```
<160> NUMBER OF SEQ ID NOS: 4

<210> SEQ ID NO 1
<211> LENGTH: 7130
<212> TYPE: DNA
<213> ORGANISM: Artificial
<220> FEATURE:
<223> OTHER INFORMATION: Synthesized

<400> SEQUENCE: 1
ttcttgaaga cgaaagggcc tcgtgatacg cctatttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtat gagtattcaa catttccgtg tcgcccttat     240 tcccttttt gcggcatttt gccttcctgt ttttgctcac ccagaaacgc tggtgaaagt     300
aaaagatgct gaagatcagt tgggtgcacg agtgggttac atcgaactgg atctcaacag     360
cggtaagatc cttgagagtt ttcgccccga agaacgtttt ccaatgatga gcacttttaa     420
agttctgcta tgtggcgcgg tattatcccg tgttgacgcc gggcaagagc aactcggtcg     480
ccgcatacac tattctcaga atgacttggt tgagtactca ccagtcacag aaaagcatct     540
tacggatggc atgacagtaa gagaattatg cagtgctgcc ataaccatga gtgataacac     600
tgcggccaac ttacttctga caacgatcgg aggaccgaag gagctaaccg cttttttgca     660
caacatgggg gatcatgtaa ctcgccttga tcgttgggaa ccggagctga atgaagccat     720
accaaacgac gagcgtgaca ccacgatgcc tgcagcaatg caacaacgt tgcgcaaact     780 attaactggc gaactactta ctctagcttc ccggcaacaa ttaatagact ggatggaggc     840
ggataaagtt gcaggaccac ttctgcgctc ggcccttccg gctggctggt ttattgctga     900
```

```
taaatctgga gccggtgagc gtgggtctcg cggtatcatt gcagcactgg ggccagatgg      960
taagccctcc cgtatcgtag ttatctacac gacggggagt caggcaacta tggatgaacg     1020
aaatagacag atcgctgaga taggtgcctc actgattaag cattggtaac tgtcagacca     1080
agtttactca tatatacttt agattgattt aaaacttcat ttttaattta aaaggatcta     1140
ggtgaagatc cttttcgata atctcatgac caaaatccct taacgtgagt tttcgttcca     1200
ctgagcgtca gacccgtag aaaagatcaa aggatcttct tgagatcctt ttttctgcg       1260
cgtaatctgc tgcttgcaaa caaaaaaacc accgctacca gcggtggttt gtttgccgga     1320
tcaagagcta ccaactcttt ttccgaaggt aactggcttc agcagagcgc agataccaaa     1380
tactgtcctt ctagtgtagc cgtagttagg ccaccacttc aagaactctg tagcaccgcc     1440
tacatacctc gctctgctaa tcctgttacc agtggctgct gccagtggcg ataagtcgtg     1500
tcttaccggg ttggactcaa gacgatagtt accggataag gcgcagcggt cgggctgaac     1560
ggggggttcg tgcacacagc ccagcttgga gcgaacgacc tacaccgaac tgagatacct     1620
acagcgtgag ctatgagaaa gcgccacgct tcccgaaggg agaaaggcgg acaggtatcc     1680
ggtaagcggc agggtcggaa caggagagcg cacgagggag cttccagggg gaaacgcctg     1740
gtatctttat agtcctgtcg ggtttcgcca cctctgactt gagcgtcgat ttttgtgatg     1800
ctcgtcaggg gggcggagcc tatggaaaaa cgccagcaac gcggcctttt tacggttcct     1860
ggccttttgc tggccttttg ctcacatgtt ctttcctgcg ttatccctg attctgtgga     1920
taaccgtatt accgcctttg agtgagctga taccgctcgc cgcagccgaa cgaccgagcg     1980
cagcgagtca gtgagcgagg aagcggaaga gcgcctgatg cggtattttc tccttacgca     2040
tctgtgcggt atttcacacc gcatatatgg tgcactctca gtacaatctg ctctgatgcc     2100
gcatagttaa gccagtatac actccgctat cgctacgtga ctgggtcatg gctgcgcccc     2160
gacacccgcc aacacccgct gacgcgccct gacgggcttg tctgctcccg gcatccgctt     2220
acagacaagc tgtgaccgtc tccgggagct gcatgtgtca gaggttttca ccgtcatcac     2280
cgaaacgcgc gaggcagctg cggtaaagct catcagcgtg gtcgtgaagc gattcacaga     2340
tgtctgcctg ttcatccgcg tccagctcgt tgagtttctc cagaagcgtt aatgtctggc     2400
ttctgataaa gcgggccatg ttaagggcgg ttttttcctg tttggtcact gatgcctccg     2460
tgtaagggg atttctgttc atgggggtaa tgataccgat gaaacgagag aggatgctca     2520
cgatacgggt tactgatgat gaacatgccc ggttactgga acgttgtgag ggtaaacaac     2580
tggcggtatg gatgcggcgg gaccagagaa aaatcactca gggtcaatgc cagcgcttcg     2640
ttaatacaga tgtaggtgtt ccacagggta gccagcagca tcctgcgatg cagatccgga     2700
acataatggt gcagggcgct gacttccgcg tttccagact ttacgaaaca cggaaaccga     2760
agaccattca tgttgttgct caggtcgcag acgttttgca gcagcagtcg cttcacgttc     2820
gctcgcgtat cggtgattca ttctgctaac cagtaaggca accccgccag cctagccggg     2880
tcctcaacga caggagcacg atcatgcgca cccgtggcca ggacccaacg ctgcccgaga     2940
tgcgccgcgt gcggctgctg gagatggcgg acgcgatgga tatgttctgc caagggttgg     3000
tttgcgcatt cacagttctc cgcaagaatt gattggctcc aattcttgga gtggtgaatc     3060
cgttagcgag gtgccgccgg cttccattca ggtcgaggtg gcccggctcc atgcaccgcg     3120
acgcaacgcg gggaggcaga caaggtatag ggcggcgcct acaatccatg ccaacccgtt     3180
ccatgtgctc gccgaggcgg cataaatcgc cgtgacgatc agcggtccag tgatcgaagt     3240
taggctggta agagccgcga gcgatccttg aagctgtccc tgatggtcgt catctacctg     3300
```

```
cctggacagc atggcctgca acgcgggcat cccgatgccg ccggaagcga agaatcat    3360
aatgggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt  3480
gacgaaggct tgagcgaggg cgtgcaagat tccgaatacc gcaagcgaca ggccgatcat  3540
cgtcgcgctc cagcgaaagc ggtcctcgcc gaaaatgacc cagagcgctg ccggcacctg  3600
tcctacgagt tgcatgataa agaagacagt cataagtgcg gcgacgatag tcatgccccg  3660
cgcccaccgg aaggagctga ctgggttgaa ggctctcaag ggcatcggtc gagatcccgg  3720
tgcctaatga gtgagctaac ttacattaat tgcgttgcgc tcactgcccg ctttccagtc  3780
gggaaacctg tcgtgccagc tgcattaatg aatcggccaa cgcgcgggga gaggcggttt  3840
gcgtattggg cgccagggtg gtttttcttt tcaccagtga cgggcaac agctgattgc    3900
ccttcaccgc ctggccctga gagagttgca gcaagcggtc cacgctggtt gccccagca   3960
ggcgaaaatc ctgtttgatg gtggttaacg gcgggatata acatgagctg tcttcggtat  4020
cgtcgtatcc cactaccgag atatccgcac caacgcgcag cccggactcg gtaatggcgc  4080
gcattgcgcc cagcgccatc tgatcgttgg caaccagcat cgcagtggga acgatgccct  4140
cattcagcat ttgcatggtt tgttgaaaac cggacatggc actccagtcg ccttcccgtt  4200
ccgctatcgg ctgaatttga ttgcgagtga gatatttatg ccagccagcc agacgcagac  4260
gcgccgagac agaacttaat gggcccgcta acagcgcgat ttgctggtga cccaatgcga  4320
ccagatgctc cacgcccagt cgcgtaccgt cttcatggga gaaataata ctgttgatgg   4380
gtgtctggtc agagacatca agaaataacg ccggaacatt agtgcaggca gcttccacag  4440
caatggcatc ctggtcatcc agcggatagt taatgatcag cccactgacg cgttgcgcga  4500
gaagattgtg caccgccgct ttacaggctt cgacgccgct tcgttctacc atcgacacca  4560
ccacgctggc acccagttga tcggcgcgag atttaatcgc cgcgacaatt tgcgacggcg  4620
cgtgcagggc cagactggag gtggcaacgc caatcagcaa cgactgtttg cccgccagtt  4680
gttgtgccac gcggttggga atgtaattca gctccgccat cgccgcttcc actttttccc  4740
gcgttttcgc agaaacgtgg ctggcctggt tcaccacgcg ggaaacggtc tgataagaga  4800
caccggcata ctctgcgaca tcgtataacg ttactggttt cacattcacc accctgaatt  4860
gactctcttc cgggcgctat catgccatac cgcgaaaggt tttgcgccat tcgatggtgt  4920
ccgggatctc gacgctctcc cttatgcgac tcctgcatta ggaagcagcc cagtagtagg  4980
ttgaggccgt tgagcaccgc cgccgcaagg aatggtgcat gcaaggagat ggcgcccaac  5040
agtcccccgg ccacggggcc tgccaccata cccacgccga acaagcgct catgagcccg    5100
aagtggcgag cccgatcttc cccatcggtg atgtcgcgca taggcgcc agcaaccgca    5160
cctgtggcgc cggtgatgcc ggccacgatg cgtccggcgt agaggatcga gatctcgatc  5220
ccgcgaaatt aatacgactc actataggg aattgtgagc ggataacaat tcccctctag   5280
aaataattt gtttaacttt aagaaggaga tataccatga aagcgatctt aatcccattt   5340
ttatctcttc tgattccgtt aaccccgcaa tctgcattcg ctcagagtga gccggagctg  5400
aagctggaaa tgtggtgat tgtcagtcgt catggtgtg gtgctccaac caaggccacg    5460
caactgatgc aggatgtcac cccagacgca tggccaacct ggccggtaaa actgggttgg  5520
ctgacaccgc gcgtggtga gctaatcgcc tatctcggac attaccaacg ccagcgtctg  5580
gtagccgacg gattgctggc gaaaagggc tgcccgcagt ctggtcaggt cgcgattatt  5640
```

-continued

```
gctgatgtcg acgagcgtac ccgtaaaaca ggcgaagcct tcgccgccgg gctggcacct    5700
gactgtgcaa taaccgtaca tacccaggca gatacgtcca gtcccgatcc gttatttaat    5760
cctctaaaaa ctggcgtttg ccaactggat aacgcgaacg tgactgacgc gatcctcagc    5820
agggcaggag ggtcaattgc tgactttacc gggcatcggc aaacggcgtt tcgcgaactg    5880
gaacgggtgc ttaattttcc gcaatcaaac ttgtgcctta aacgtgagaa acaggacgaa    5940
agctgttcat taacgcaggc attaccatcg gaactcaagg tgagcgccga caatgtctca    6000
ttaaccggtg cggtaagcct cgcatcaatg ctgacggaga tatttctcct gcaacaagca    6060
cagggaatgc cggagccggg gtggggaagg atcaccgatt cacaccagtg gaacaccttg    6120
ctaagtttgc ataacgcgca atttttatttg ctacaacgca cgccagaggt tgcccgcagc    6180
cgcgccaccc cgttattgga tttgatcatg gcagcgttga cgccccatcc accgcaaaaa    6240
caggcgtatg gtgtgacatt acccacttca gtactgttta ttgccggaca cgatactaat    6300
ctggcaaatc tcggcggcgc actggagctc aactggacgc ttcccggtca gccggataac    6360
acgccgccag gtggtgaact ggtgtttgaa cgctggcgtc ggctaagcga taacagccag    6420
tggattcagg tttcgctggt cttccagact ttacagcaga tgcgtgataa aacgccgctg    6480
tcattaaata cgccgcccgg agaggtgaaa ctgaccctgg caggatgtga agagcgaaat    6540
gcgcagggca tgtgttcgtt ggcaggtttt acgcaaatcg tgaatgaagc acgcataccg    6600
gcgtgcagtt tgggaggttc aggcggttct ggtggatctt cggatattct ttacggtgac    6660
atcaatctgg acggaaaaat taactcttca gatgttacac tgttaaaaag atatattgtg    6720
aagtccatag atgttttccc aaccgctgat ccggaacgga gcttaatagc atcagatgta    6780
aacggagacg gaagggtaaa ctctacagac tattcatacc ttaaacgtta tgtcttgaaa    6840
atcataccaa ccatacccgg aaattcatga ctagcataac cccttggggc tctaaacgg    6900
gtcttgaggg gttttttgct gaaaggagga actatatccg gatatcccgc aagaggcccg    6960
gcagtaccgg cataaccaag cctatgccta cagcatccag ggtgacggtg ccgaggatga    7020
cgatgagcgc attgttagat ttcatacacg gtgcctgact gcgttagcaa tttaactgtg    7080
ataaactacc gcattaaagc ttatcgatga taagctgtca acatgagaa                7130
```

<210> SEQ ID NO 2
<211> LENGTH: 517
<212> TYPE: PRT
<213> ORGANISM: Artificial
<220> FEATURE:
<223> OTHER INFORMATION: Synthesized

<400> SEQUENCE: 2

```
Met Lys Ala Ile Leu Ile Pro Phe Leu Ser Leu Leu Ile Pro Leu Thr
1               5                   10                  15

Pro Gln Ser Ala Phe Ala Gln Ser Glu Pro Glu Leu Lys Leu Glu Ser
            20                  25                  30

Val Val Ile Val Ser Arg His Gly Val Arg Ala Pro Thr Lys Ala Thr
        35                  40                  45

Gln Leu Met Gln Asp Val Thr Pro Asp Ala Trp Pro Thr Trp Pro Val
    50                  55                  60

Lys Leu Gly Trp Leu Thr Pro Arg Gly Gly Glu Leu Ile Ala Tyr Leu
65                  70                  75                  80

Gly His Tyr Gln Arg Gln Arg Leu Val Ala Asp Gly Leu Leu Ala Lys
                85                  90                  95
```

```
Lys Gly Cys Pro Gln Ser Gly Gln Val Ala Ile Ile Ala Asp Val Asp
            100                 105                 110

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
            130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Ser Ile Ala Asp
                165                 170                 175

Phe Thr Gly His Arg Gln Thr Ala Phe Arg Glu Leu Glu Arg Val Leu
            180                 185                 190

Asn Phe Pro Gln Ser Asn Leu Cys Leu Lys Arg Glu Lys Gln Asp Glu
            195                 200                 205

Ser Cys Ser Leu Thr Gln Ala Leu Pro Ser Glu Leu Lys Val Ser Ala
            210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
            260                 265                 270

Asn Ala Gln Phe Tyr Leu Leu Gln Arg Thr Pro Glu Val Ala Arg Ser
            275                 280                 285

Arg Ala Thr Pro Leu Leu Asp Leu Ile Met Ala Ala Leu Thr Pro His
            290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
            340                 345                 350

Gly Glu Leu Val Phe Glu Arg Trp Arg Leu Ser Asp Asn Ser Gln
            355                 360                 365

Trp Ile Gln Val Ser Leu Val Phe Gln Thr Leu Gln Gln Met Arg Asp
370                 375                 380

Lys Thr Pro Leu Ser Leu Asn Thr Pro Pro Gly Glu Val Lys Leu Thr
385                 390                 395                 400

Leu Ala Gly Cys Glu Glu Arg Asn Ala Gln Gly Met Cys Ser Leu Ala
                405                 410                 415

Gly Phe Thr Gln Ile Val Asn Glu Ala Arg Ile Pro Ala Cys Ser Leu
            420                 425                 430

Gly Gly Ser Gly Gly Ser Gly Ser Ser Asp Ile Leu Tyr Gly Asp
            435                 440                 445

Ile Asn Leu Asp Gly Lys Ile Asn Ser Ser Asp Val Thr Leu Leu Lys
            450                 455                 460

Arg Tyr Ile Val Lys Ser Ile Asp Val Phe Pro Thr Ala Asp Pro Glu
465                 470                 475                 480

Arg Ser Leu Ile Ala Ser Asp Val Asn Gly Asp Gly Arg Val Asn Ser
                485                 490                 495

Thr Asp Tyr Ser Tyr Leu Lys Arg Tyr Val Leu Lys Ile Pro Thr
            500                 505                 510
```

```
Ile Pro Gly Asn Ser
        515

<210> SEQ ID NO 3
<211> LENGTH: 9
<212> TYPE: PRT
<213> ORGANISM: Artificial
<220> FEATURE:
<223> OTHER INFORMATION: Synthesized

<400> SEQUENCE: 3

Gly Gly Ser Gly Gly Ser Gly Gly Ser
1               5

<210> SEQ ID NO 4
<211> LENGTH: 18
<212> TYPE: PRT
<213> ORGANISM: Artificial
<220> FEATURE:
<223> OTHER INFORMATION: Synthesized

<400> SEQUENCE: 4

Gly Gly Ser Gly Gly Ser Gly Gly Ser Gly Gly Ser Gly Gly Ser Gly
1               5                   10                  15

Gly Ser
```